US00PP18586P2

(12) United States Plant Patent
Buffinga

(10) Patent No.: US PP18,586 P2
(45) Date of Patent: Mar. 11, 2008

(54) ***HIBISCUS* PLANT NAMED 'HJ-116'**

(50) Latin Name: *Hibiscus rosa-sinensis*
Varietal Denomination: HJ-116

(76) Inventor: Henry Albert Buffinga, RR #2, Seaforth, Ontario (CA), N0K 1W0

( * ) Notice: Subject to any disclaimer, the term of this patent is extended or adjusted under 35 U.S.C. 154(b) by 0 days.

(21) Appl. No.: 11/591,011

(22) Filed: Nov. 1, 2006

(51) Int. Cl.
*A01H 5/00* (2006.01)

(52) U.S. Cl. ..... Plt./257
(58) Field of Classification Search ..... Plt./257
See application file for complete search history.

(56) References Cited

PUBLICATIONS

UPOV ROM GTITM Computer Database, GTI Jouve Retrieval Software 2007/02 Ciations for 'hj–116'.*

* cited by examiner

*Primary Examiner*—Wendy Haas
(74) *Attorney, Agent, or Firm*—C. A. Whealy

(57) ABSTRACT

A new and distinct cultivar of *Hibiscus* plant named 'HJ-116', characterized by its upright and somewhat outwardly spreading plant habit; freely branching habit when pinched; relatively large leaves; large pale yellow-colored flowers with red-colored centers; and long flower longevity.

2 Drawing Sheets

Botanical designation: *Hibiscus rosa-sinensis.*
Cultivar denomination: 'HJ-116'.

BACKGROUND OF THE INVENTION

The present invention relates to a new and distinct cultivar of *Hibiscus,* botanically known as *Hibiscus rosa-sinensis,* and hereinafter referred to by the name 'HJ-116'.

The new *Hibiscus* is a product of a planned breeding program conducted by the Inventor in Seaforth, Ontario, Canada. The objective of the breeding program is to create new *Hibiscus* cultivars that flower early and have long flower longevity.

The new *Hibiscus* originated from a cross-pollination made by the Inventor in Seaforth, Ontario, Canada in November, 2002, of the *Hibiscus rosa-sinensis* cultivar Byron Metts, not patented, as the female, or seed, parent with a proprietary *Hibiscus rosa-sinensis* selection, designated as code number HJ-136, not patented, as the male, or pollen, parent. The cultivar HJ-116 was discovered and selected by the Inventor as a single flowering plant within the progeny of the stated cross-pollination in a controlled environment in Seaforth, Ontario, Canada in October, 2003.

Asexual reproduction of the new *Hibiscus* by vegetative terminal cuttings in a controlled environment in Seaforth, Ontario, Canada since October, 2003, has shown that the unique features of this new *Hibiscus* are stable and reproduced true to type in successive generations.

SUMMARY OF THE INVENTION

The cultivar HJ-116 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'HJ-116'.

These characteristics in combination distinguish 'HJ-116' as a new and distinct cultivar of *Hibiscus:*

1. Upright and somewhat outwardly spreading plant habit.
2. Freely branching habit when pinched.
3. Relatively large leaves.
4. Large pale yellow-colored flowers with red-colored centers.
5. Long flower longevity.

Plants of the new *Hibiscus* can be compared to plants of the female parent, the cultivar Byron Metts. Plants of the new *Hibiscus* differ from plants of the cultivar Byron Metts in the following characteristics:

1. Plants of the new *Hibiscus* have smaller and lighter green-colored leaves than plants of the cultivar Byron Metts.
2. Plants of the new *Hibiscus* have smaller flowers than plants of the cultivar Byron Metts.
3. Plants of the new *Hibiscus* and the cultivar Byron Metts differ in flower coloration as plants of the cultivar Byron Metts have solid white-colored flowers.

Plants of the new *Hibiscus* can be compared to plants of the male parent, the proprietary *Hibiscus* selection code number HJ-136. Plants of the new *Hibiscus* differ from plants of the male parent selection in the following characteristics:

1. Plants of the new *Hibiscus* have smaller leaves than plants of the male parent selection.
2. Plants of the new *Hibiscus* and the male parent selection differ in flower coloration as plants of the male parent selection have white and purple-colored flowers.
3. Plants of the new *Hibiscus* have longer lasting flowers than plants of the male parent selection.

Plants of the new *Hibiscus* can be compared to plants of the *Hibiscus rosa-sinensis* cultivar Coconut Cream, not patented. In side-by-side comparisons conducted in Seaforth, Ontario, Canada, plants of the new *Hibiscus* differed from plants of the cultivar Coconut Cream in the following characteristics:

1. Plants of the new *Hibiscus* had leaves with obtuse bases and crenate margins whereas plants of the cultivar Coconut Cream had leaves with cordate bases and weakly crenate margins.
2. Plants of the new *Hibiscus* had longer leaf petioles than plants of the cultivar Coconut Cream.
3. Plants of the new *Hibiscus* had less undulating petal margins than plants of the cultivar Coconut Cream.
4. Flowers of plants of the new *Hibiscus* and the cultivar Coconut Cream differed in flower color as plants of the cultivar Coconut Cream did not have red-colored centers.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus*.

The photograph on the first sheet comprises a side perspective view of typical flowering plants of 'HJ-116' grown in a container.

The photograph on the second sheet comprises a close-up view of a typical flower of 'HJ-116' (left) and 'Coconut Cream' (right).

DETAILED BOTANICAL DESCRIPTION

The photographs and following observations, measurements and values describe plants grown in Seaforth, Ontario, Canada in containers in polyethylene-covered greenhouses under conditions which closely approximate commercial production. During the production of the plants, day temperatures ranged from about 20° C. to about 35° C. and night temperatures ranged from about 18° C. to about 21° C. Plants were about ten months old when the photographs and the description were taken. In the description, color references are made to The Royal Horticultural Society Colour Chart, 1995 Edition, except where general terms of ordinary dictionary significance are used.

Botanical classification: *Hibiscus rosa-sinensis* cultivar HJ-116.

Parentage:

*Female, or seed, parent.*—*Hibiscus rosa-sinensis* cultivar Byron Metts, not patented.

*Male or pollen parent.*—Proprietary selection of *Hibiscus rosa-sinensis* designated as code number HJ-136, not patented.

Propagation:

*Type.*—By vegetative terminal cuttings.

*Time to initiate roots.*—About two weeks.

*Time to develop roots.*—About four weeks.

*Root description.*—Thick, fleshy; white in color.

*Rooting habit.*—Freely branching; moderately dense.

Plant description:

*Plant form and growth habit.*—Upright and somewhat outwardly spreading plant habit. Moderately vigorous growth habit. Branching habit: Freely branching, usually about three to four lateral branches develop after pinching (removal of terminal apex).

*Plant height.*—About 46.6 cm.

*Plant diameter* (*area of spread*).—About 50 cm.

Lateral branch description:

*Length.*—About 35 cm.

*Diameter.*—About 6 mm.

*Internode length.*—About 2 cm.

*Texture.*—Immature, sparsely pubescent; mature, woody and rough.

*Color, immature.*—143C.

*Color, mature.*—197C.

Foliage description:

*Arrangement.*—Alternate, single.

*Length.*—About 10.2 cm.

*Width.*—About 9.4 cm.

*Shape.*—Ovate.

*Apex.*—Acute to bluntly acuminate.

*Base.*—Obtuse.

*Margin.*—Crenate; undulating.

*Texture, upper and lower surfaces.*—Smooth, glabrous; slightly rugose.

*Venation pattern.*—Palmate.

*Color.*—Developing foliage, upper surface: 146A. Developing foliage, lower surface: 146B. Mature foliage, upper surface: Close to 139A; venation, similar to lamina. Mature foliage, lower surface: Close to 137B; venation, similar to lamina.

*Petiole.*—Length: About 4.8 cm. Diameter: About 3 mm. Texture, upper and lower surfaces: Smooth, glabrous. Color, upper surface: 137A. Color, lower surface: 137B.

Flower description:

*Flower arrangement.*—Flowers arranged singly at terminal leaf axils. Uniform and freely flowering habit with usually about three or four flower buds and/or open flowers per terminal apex. Flowers face mostly upright to slightly outwardly.

*Flowering appearance.*—Rounded, pale yellow-colored flowers with red-colored centers.

*Flower longevity.*—Flowers are long lasting, lasting for about two to six days. Flowers persistent.

*Natural flowering season.*—Usually spring and summer or during periods of warm weather.

*Flower diameter.*—About 17.4 cm.

*Flower length* (*height*).—About 11 cm.

*Flower bud.*—Length: About 8.5 cm. Diameter: About 3 cm. Shape: Elliptic. Color: 151D.

*Petals.*—Arrangement: Corolla consists of five imbricate petals. Length: About 10.2 cm. Width: About 9.4 cm. Shape: Spatulate. Apex: Rounded. Base: Attenuate. Margin: Entire; moderately undulate; ruffled appearance. Texture, upper and lower surfaces: Smooth, glabrous, satiny. Color: When opening and fully opened, upper surface: Towards the apex, 5D to 4D; mid-section, close to 155A; towards the base, 46B to 45C. When opening and fully opened, lower surface: Close to 155B; towards the base, blushed with 46B to 45C.

*Sepals.*—Appearance: Five sepals fused into a star-shaped calyx. Length: About 2.5 cm to 3 cm. Width: About 1 cm to 1.5 cm. Shape: Deltoid to ovate. Apex: Acuminate. Margin: Entire. Texture, upper and lower surfaces: Smooth, glabrous. Color, upper surface: 144B. Color, lower surface: 144A to 144B.

*Bracts.*—Appearance: About seven or eight fused at base. Length: About 2.2 cm. Width: About 6 mm. Shape: Linear. Apex: Acuminate. Margin: Entire. Texture, upper and lower surfaces: Smooth, glabrous. Color, upper and lower surfaces: Close to 147A.

*Peduncles.*—Length: About 4 cm. Diameter: About 4 mm. Strength: Strong, flexible. Texture: Smooth, glabrous. Color: 144A.

*Reproductive organs.*—Androecium: Stamen number: Numerous, about 60. Filament length: About 4 mm. Filament color: Close to 155A. Anther shape: Reniform. Anther length: About 1.5 mm. Anther color: Close to 15B. Amount of pollen: Abundant. Pollen color: Close to 15B. Gynoecium: Pistil length: About 10.5 cm. Style length: About 10 cm. Style texture: Smooth, waxy. Style color: Towards the apex, close to 4D; towards the base, tinted with close to 45B. Stigma appearance: Five, rounded. Stigma diameter: About 2 mm. Stigma color: 14B. Ovary color: Close to 154D.

*Seed/fruit.*—Seed and fruit production has not been observed.

Temperature tolerance: Plants of the new *Hibiscus* have been observed to tolerate temperatures from about 10° C. to about 35° C.

Pathogen/pest resistance: Plants of the new *Hibiscus* have not been shown to be tolerant to pathogens and pests common to *Hibiscus*.

It is claimed:

1. A new and distinct *Hibiscus* plant named 'HJ-116' as illustrated and described.

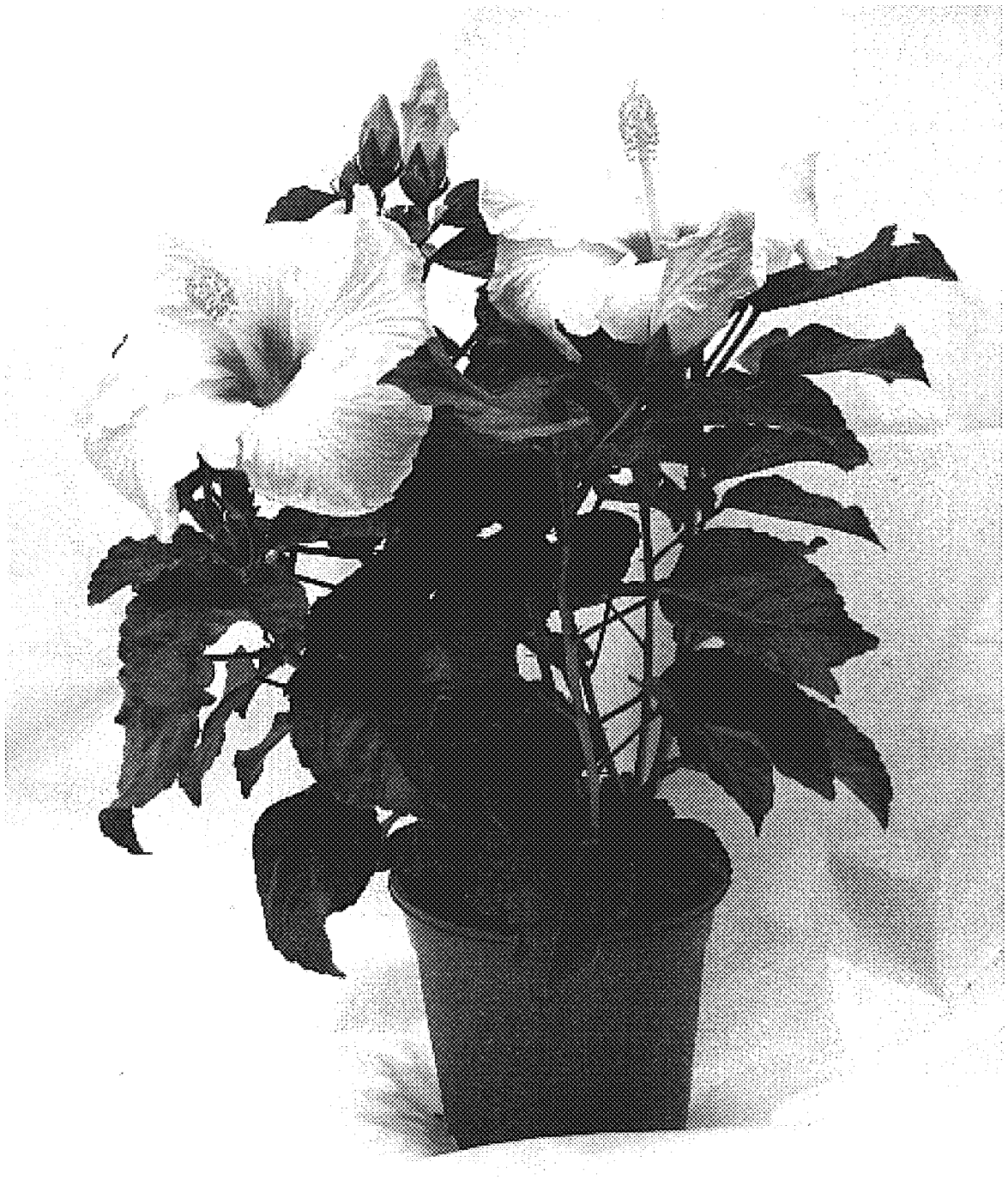

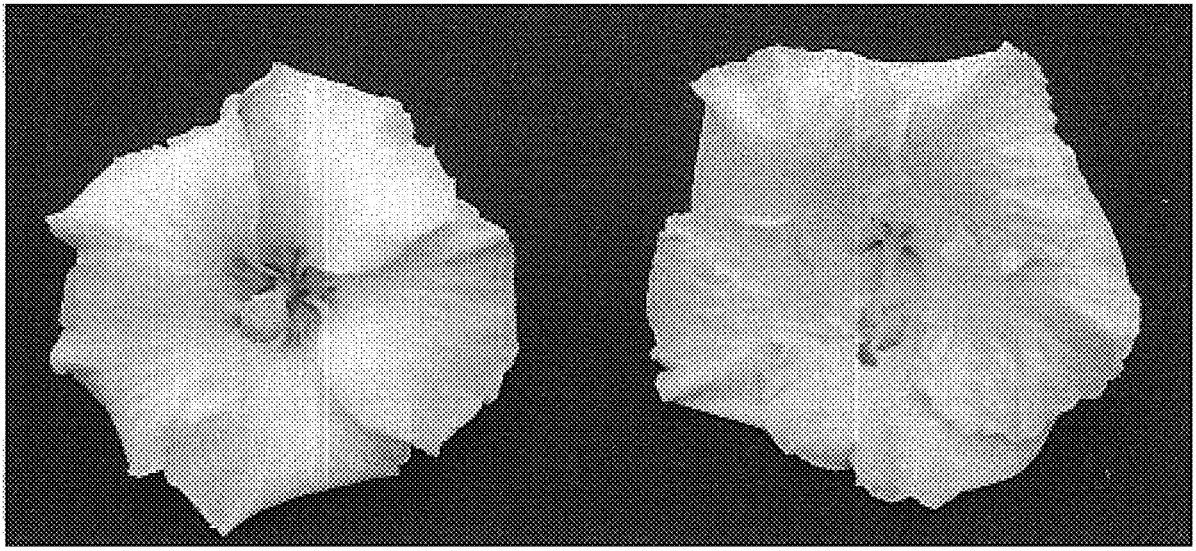

* * * * *